(12) United States Patent
Maret

(10) Patent No.: US 11,872,687 B2
(45) Date of Patent: *Jan. 16, 2024

(54) FORCE BASED GESTURE CONTROL OF A ROBOTIC SURGICAL MANIPULATOR

(71) Applicant: Asensus Surgical US, Inc., Durham, NC (US)

(72) Inventor: Alexander John Maret, Durham, NC (US)

(73) Assignee: Asensus Surgical US, Inc., Durham, NC (US)

( * ) Notice: Subject to any disclaimer, the term of this patent is extended or adjusted under 35 U.S.C. 154(b) by 30 days.

This patent is subject to a terminal disclaimer.

(21) Appl. No.: 17/505,564

(22) Filed: Oct. 19, 2021

(65) Prior Publication Data

US 2022/0032473 A1 Feb. 3, 2022

Related U.S. Application Data

(63) Continuation of application No. 16/236,613, filed on Dec. 30, 2018, now Pat. No. 11,148,297.

(60) Provisional application No. 62/612,556, filed on Dec. 31, 2017.

(51) Int. Cl.
*B25J 13/08* (2006.01)
*A61B 34/30* (2016.01)
*A61B 34/00* (2016.01)
*B25J 17/02* (2006.01)
*A61B 34/37* (2016.01)
*A61B 90/00* (2016.01)

(52) U.S. Cl.
CPC ............ *B25J 13/085* (2013.01); *A61B 34/30* (2016.02); *A61B 34/37* (2016.02); *A61B 34/74* (2016.02); *A61B 34/76* (2016.02); *B25J 17/025* (2013.01); *A61B 2034/301* (2016.02); *A61B 2034/302* (2016.02); *A61B 2090/064* (2016.02); *A61B 2090/066* (2016.02)

(58) Field of Classification Search
CPC ...... B25J 13/085; B25J 9/1633; B25J 9/1694; A61B 34/30; A61B 34/76; A61B 34/35; A61B 2034/301; A61B 2034/302; A61B 2090/064; A61B 2090/066
See application file for complete search history.

(56) References Cited

U.S. PATENT DOCUMENTS

2004/0034283 A1\* 2/2004 Quaid, III ............ A61B 34/76
600/300
2009/0076476 A1 3/2009 Barbagli et al.
2010/0204713 A1 8/2010 Ruiz Morales
2012/0283747 A1 11/2012 Popovic
(Continued)

FOREIGN PATENT DOCUMENTS

WO 2017220822 A1 12/2017

*Primary Examiner* — Khoi H Tran
*Assistant Examiner* — Tanner L Cullen

(57) ABSTRACT

A method of controlling a robotic arm in a surgical system comprises manually applying a force to a body of the robotic arm. Force information is received from ae force sensor on the robotic arm and a controller determines, using the force information, whether the force is a gesture force input. If the force is determined to be a gesture force input, the controller initiates electromechanical movement of the manipulator arm to a draping configuration, instrument attachment configuration, storage configuration, or home configuration.

12 Claims, 7 Drawing Sheets

(56) References Cited

U.S. PATENT DOCUMENTS

| | | |
|---|---|---|
| 2014/0371762 A1 | 12/2014 | Farritor et al. |
| 2016/0184032 A1 | 6/2016 | Romo et al. |
| 2018/0064492 A1 | 3/2018 | Lightcap et al. |
| 2018/0154519 A1* | 6/2018 | Lin ................. B25J 13/085 |
| 2018/0210434 A1* | 7/2018 | Iwatake ............ B25J 9/0081 |
| 2019/0022857 A1 | 1/2019 | Conus et al. |
| 2019/0176334 A1 | 6/2019 | Zhou et al. |
| 2020/0375672 A1* | 12/2020 | Penny ................ A61B 34/77 |

* cited by examiner

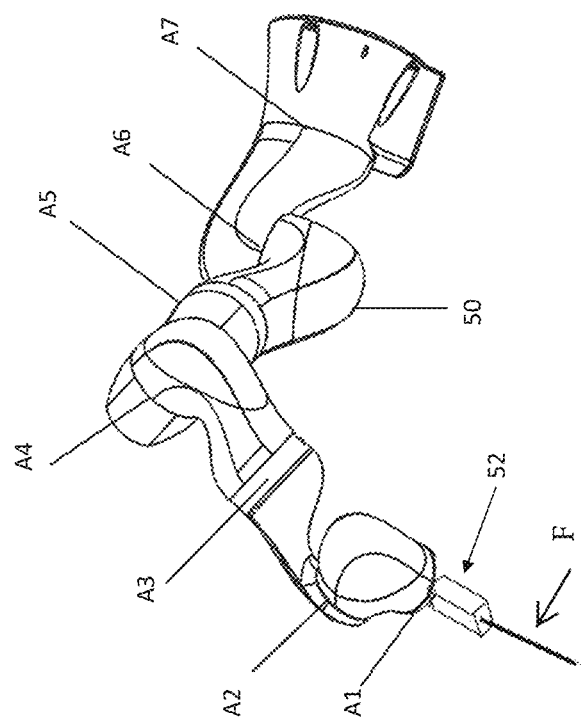

FORCE BASED GESTURE CONTROL OF A ROBOTIC SURGICAL MANIPULATOR

This application is a continuation of U.S. application Ser. No. 16/236,613, filed Dec. 30, 2018 which claims the benefit of U.S. Provisional Application No. 62/612,556, filed Dec. 31, 2017, each of which is incorporated herein by reference.

BACKGROUND

Commercially available surgical robotic systems use a plurality of robotic arms. The arms may be positioned on separate bases independently moveable within an operating room, or on a common base, or on other fixtures within the operating room, such as the patient table or a ceiling mounted fixture. Each arm carries a surgical instrument, or a camera that is used to capture images from within the body for display on a monitor. See U.S. Pat. No. 9,358,682. The arms electromechanically position and/or orient the camera and instruments and, where applicable, actuate the instruments. Typical configurations allow two or three instruments and the camera to be supported and manipulated by the system. Input to the system is generated based on input from a surgeon positioned at a master console, typically using input devices such as input handles and a foot pedal and, in some cases eye gaze input. Motion and actuation of the surgical instruments and the camera is controlled based on the user input. The image captured by the camera is shown on a display at the surgeon console. The console may be located patient-side, within the sterile field, or outside of the sterile field.

For a given surgical robotic system, there are certain steps involving movement of the manipulator arms that may be routinely used. For example, there are certain movements that are frequently needed during set-up of the system prior to surgery, such as to configure the system to allow it to be covered by sterile drapes. Other movements are used to configure the system for storage between surgeries. Still other movements might be needed during the course of the surgery.

This application describes features that improve the usability of the robotic system by enabling the users to control some of the functionality of the robotic manipulator. In the disclosed embodiments, commands are given to the system using force-based gesture control, allowing the user to simply push on the robot in a unique way to command the desired change to the system.

BRIEF DESCRIPTION OF THE DRAWINGS

FIG. 2 is a perspective view of an alternative robotic arm that may be used in a system having the force-based gesture control features described herein;

DETAILED DESCRIPTION

Figure 1:
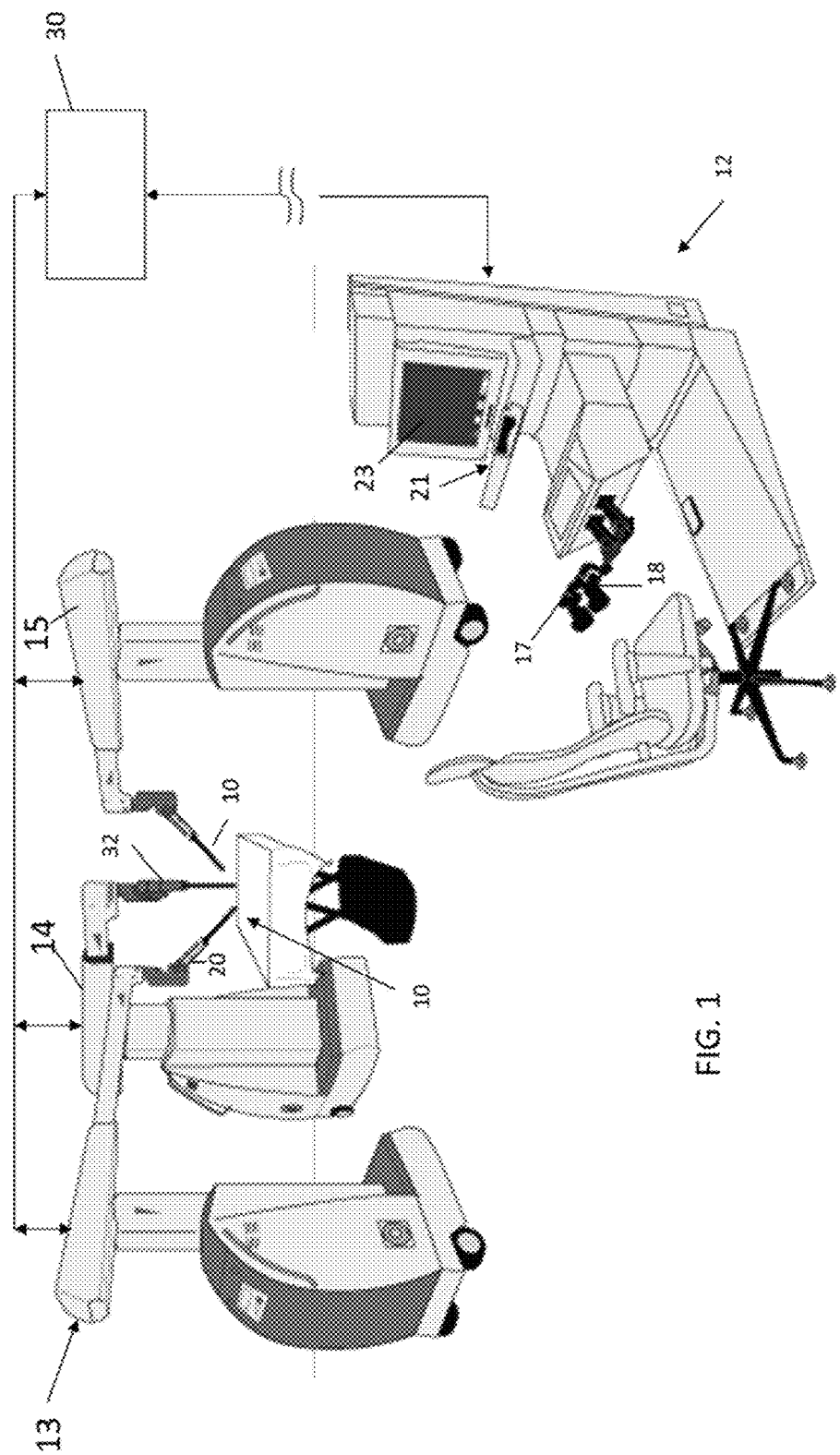
FIG. 1 is a perspective view of a surgical system, having robotic arms, that may incorporate the force-based gesture control features described herein.
Figure 5:
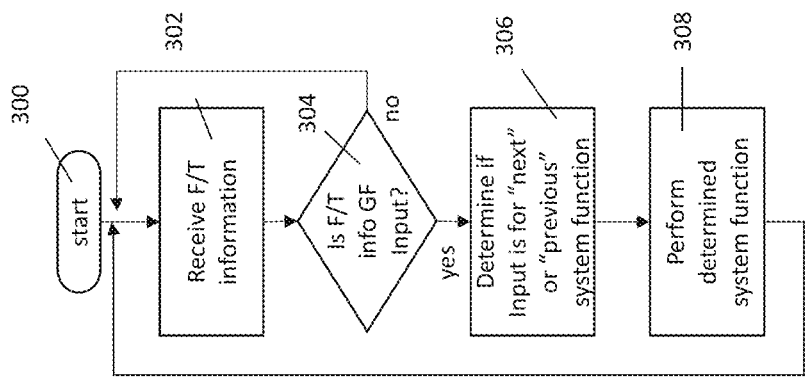
FIG. 5 is a flow diagram illustrating a third embodiment of a force-based gesture control method.

Although the inventions described herein may be used on a variety of robotic surgical systems, embodiments will be described with reference to the systems shown in FIGS. 1 and 2. The FIG. 1 system includes one or more robotic arms 13, 14, 15, each of which includes an end effector unit 20 at its distal end. The end effector unit 20 is designed to receive the proximal end of a detachable surgical instrument 10. The effector unit 20 is arranged to support the proximal end of the corresponding instrument in a mechanically rigid manner, and it is further provided with actuating means for actuating certain types of instruments. It may also include signal and power connection means for electrically connecting the instrument 10 to the system. In use, the distal end of each instrument is positioned in a body cavity of a patient, and its corresponding robotic arm is controlled by the system to position, orient, actuate (e.g. jaw open-close) the tip of the instrument within the body cavity.

A surgeon console 12 has two input devices such as handles 17, 18 that the surgeon selectively assigns to robotic arms 13, 14, 15, allowing a surgeon working at the console to control the surgical instruments 10. Where two handles are used, the surgeon can simultaneously control two of the instruments using the handles 17, 18, and control a third one of the instruments by operatively disengaging one of the handles 17, 18 from one of the initial two instruments and then operatively pairing that handle with the third instrument. One of the instruments 10, such as the instrument on arm 14, is preferably a laparoscopic camera that captures an image of the working site within the patient. An image display 23 at the console 12 displays the image captured by the camera. As described in U.S. Pat. No. 9,360,934, the system may include an eye tracker 21 that allows the surgeon to control movement of the camera by shifting his/her gaze with respect to the displayed image and/or by altering the distance between his/her eyes and the display. As described in that patent, the console may further include a human machine interface rendered on a portion of the display 23, and other input devices such as a keyboard and foot pedal.

The system includes one or more controllers 30 operationally connected to the robotic arms and to the user interface. In this description, the singular term "controller" will be used for simplicity, but it should be understood that that term is being used broadly to mean one or more controllers. The controller 30 comprises one or more computers programmed with software that, among other things, generates movement commands for operating the robotic arms based on surgeon input received from the input devices 17, 18, 21 corresponding to the desired movement of the surgical instruments 10. Associated with the controller 30 is memory programmed with instructions that cause the controller to execute a method according to which it determines whether force information received from sensors on an arm meets predetermined rules or parameters as to what constitutes gesture force input, and activates a function or changes a mode of operation or operational state of that arm in response to gesture force input.

The system is configured to allow the user to impart forces directly (i.e. against the arm itself or a sterile covering or drape on the arm) to the robotic arm by manually pushing or pulling against the arm, and to have the controller respond to such forces as input commanding the control to carry out a predetermined system function. To allow for force gesture control using the principles described below, the robotic arms include one or more gesture force sensors (GFS) that generate signals corresponding to forces or torque exerted on the robotic arms. The GFS may be one solely used by the system for gesture force input, or it may be one used by the system for other purposes such as to estimate forces at the tip of an instrument 10 during its use in a surgical procedure (e.g. for determining the haptic information needed to provide force feedback to the surgeon at the console). Sensor configurations described in U.S. Pat. No. 9,707,684 for this latter purpose may be used to receive gesture force input using the principles described in the present application. More particularly, that patent describes a 12-DOF (i.e. 12 axis) force, torque and acceleration sensor (referred to as "F/TAS"), which may be configured as single sensor unit comprising a 6-DOF force/torque sensor, ("F/T sensor") hereinafter, for sensing forces and torques on three orthogonal axes, and a built-in 6-DOF accelerometer, for sensing linear and angular acceleration about the three orthogonal axes. Alternative sensors listed in that patent include a 6-DOF F/T sensor with an appropriately associated separate 6-DOF accelerometer. The prior patent describes the sensor as is rigidly fixed to the robotic arm. For example, the sensor may have a sensing plate rigidly connected to the effector unit 20. Instead of the described F/TAS, a sensor unit comprising only a 6-DOF F/T sensor (i.e. no accelerometer) can be used. In the latter case, acceleration components can be determined using the second derivative of position coordinates of the end-effector (e.g. effector unit 20) obtained e.g. by direct kinematic computation using articulation positions. As described, compensation of dynamic loads can thus be achieved without an accelerometer.

As another alternative, the system may make use of torque and/or force sensors disposed at the joints of the robotic arms rather than the 6 DOF force/torque sensor fixed to the effector unit 20. Commonly owned WO/2017/132696, Force Estimation Using Robotic Manipulator Force Torque Sensors, filed Jan. 30, 2017, describes a robotic manipulator arm 50 of the type shown in FIG. 2, which may be supported by a cart, or mounted to the floor, ceiling mount, or patient bed. A surgical instrument 52 (which may be a laparoscopic type of instrument) is mounted to an effector unit of the arm as shown. The arm is moveable in multiple degrees of freedom which in this example are shown as seven rotational axes of the robotic arm. More particularly, the arm has a plurality of segments, each rotatable at a joint about a rotation axis. These axes are A1 through A7 in FIG. 2. A plurality of the joints, which may be each joint, includes sensors such as angular position sensors and/or torque sensors. The external loads applied to the instrument can be determined by using the measured torques and positions at each such joint, adjusting for the known effects of gravity and accelerations, as described in that application. During the operation, the forces applied by the instrument end effector can be measured and used to provide haptic feedback to the operator via the surgeon console. These sensors may also be used as gesture force sensors in accordance with the principles described in the present application.

While certain examples of GFS arrangements and features have been described, it is not intended that the scope of the inventions described herein be limited to any particular arrangement or feature, and it should be appreciated that other GFS arrangements and features not specifically described herein are encompassed within the scope of the described inventions.

The use of GFS input for certain system functions improves the usability of the robotic system by enabling users standing adjacent or in proximity to the robotic arms to control some of the functionality of the robotic manipulator. In the disclosed embodiments, a user gives commands to the system using force-based gesture control, allowing the user to simply push on an arm of the robot in a unique way to command the desired change to the system. Using force-based gesture control, the user can advance through system setup, toggle the arm between an enabled operational state (in which its movement can be command by motion of a handle 17, 18) and a disabled operational state, cycle through control modes, etc. without requiring a user to navigate through a menu on a user interface at the surgeon console or press a series of buttons located on the robotic arms or the surgeon console.

Gesture Force Input Determination and System Functions

As discussed, the system is programmed with instructions that, when executed, cause the controller to carry out a method for controlling a function of the robotic surgical system using gesture force input. Within those programmed instructions are a set of rules or parameters defining the information that is to be accepted by the system as gesture force input. Based on these rules and instructions, the controller can determine whether force/torque information received from the GFS is to be accepted as gesture force input.

As non-limiting examples, the rules or parameters in the programmed instructions may include any of the following alone or in combination with each other or with others not listed here:
  (a) the area on the robotic arm at which force/torque is being applied. The facilitate this form of input, the robotic arm may be marked with areas identifying areas at which gesture force input is to be applied. In some examples, different areas of the arm may be marked as being the gesture force input zones for certain types of input. Thus, as a specific example, one region is marked as the gesture force input zone for a first mode of operation, operational state or arm position or pose, and a second region is marked as the gesture force input zone for a second mode of operation, operational state or arm position or pose.
  (b) the direction of the applied force/torque
  (c) the frequency of the applied force/torque (e.g. a rate of between X and Y pushes per 2 second period)
  (d) the number of instances of applied force/torque over a time period (e.g. 2 pushes within a 3 second period)
  (e) the duration of application of force/torque (e.g. a duration of between 2-3 seconds)
  (f) the direction and/or distance of displacement of parts of the robotic manipulator
  (g) status or position of the robotic arm (e.g. if the robotic arm is in a disabled state, a gesture force meeting some other parameter such as those listed here is considered to be gesture force input)
  (h) stage of the surgical procedure (e.g. if other input to the system indicates that the surgical procedure is in a particular stage, a gesture force meeting some other parameter such as those listed here is considered to be a gesture force input).

The programmed instructions may additionally include instructions as to the system functions that will be commanded once force/torque information is determined to be gesture force input. Many types of system functions are contemplated. These include, but are not limited to:

(a) moving the arm to a particular predefined pose or configuration in which the joints are positioned to arrange the arm in a configuration most suitable for arm storage, arm draping, instrument mounting onto the effector unit, or as a home position for insertion of the instrument into the patient.

(b) causing the arm to withdraw an instrument tip from the patient (e.g. use of the arm to move the instrument in a proximal direction along the longitudinal axis of the instrument shaft), and/or, after replacement of a first instrument with a second instrument, advancement of the second instrument into the body cavity to position its tip in the same position and orientation possessed by the first instrument before its withdrawal.

(c) determining the fulcrum of the instrument shaft (i.e. the pivot point of the instrument at the incision site) using a process such as that described in in commonly owned U.S. Pat. No. 9,707,684, or instrument calibration tasks.

(d) changes in the system's operational state (e.g. between enabled or disabled).

(e) changes in the system's mode of operation. Examples of modes of operation include, without limitation, any of the modes described in U.S. Ser. No. 15/978,069, filed May 11, 2018, which is incorporated herein by reference, as well as the following:

Fully Compliant Mode—In this mode, the manipulator arm is in a "compliant" state in which it can be freely repositioned by the user by exerting force on the robotic arm (hand-guiding). The motors of the robotic arm may be activated to perform active gravity compensation such that the manipulator and payload float freely in space enabling the user to move the payload and manipulator without need to support the weight of the components. In this particular state, the arm and payload can be moved in any direction or orientation, only restricted by the range of motion of the robotic manipulator. In another embodiment, some of the components or axes may be supported by passive gravity compensation using mechanisms as an alternative to motor torque. This can also be thought of as a "follow me" mode, in which the robot will follow the user's guidance as s/he grabs and repositions the manipulator arm.

Figure 9B:
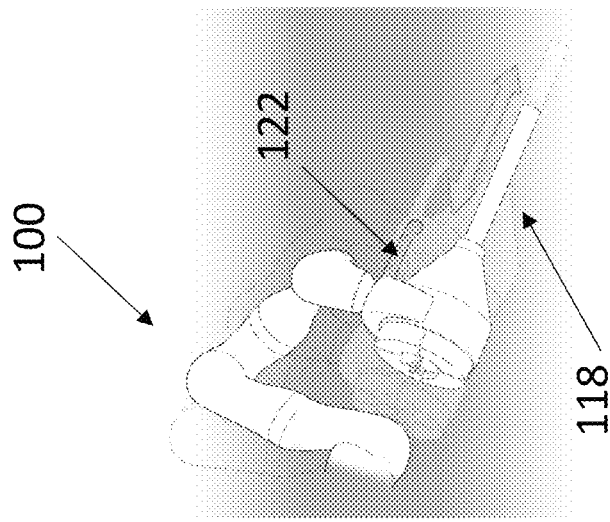
FIG. 9B illustrates the system of FIGS. 6-8C in a Z-Translate mode.
Figure 9A:
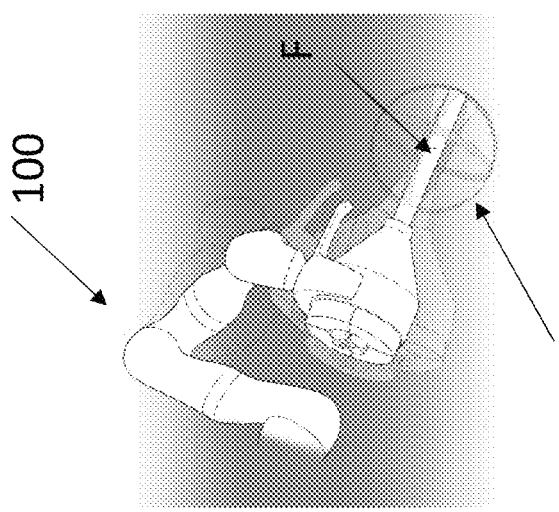
FIG. 9A illustrates the system of FIGS. 6-8C in an RCM handguiding mode.

RCM Hand-guiding—In this mode, the manipulator arm is in a "compliant" state in which it can be repositioned by the user by exerting force on the robotic arm, with some restrictions. The robotic arm's motors are used to perform active gravity compensation such that the manipulator and payload float in space enabling the user to move the payload and manipulator without need to support the weight of the components. In this particular state, the arm and payload can be moved by the user, but the robot will only allow the payload to rotate about a fixed control point (3 rotational degrees of freedom). The instrument or engine (payload) can be rotated about the fulcrum point F (FIG. 2) but cannot be translated. The payload can only be manipulated in 3 rotational degrees of freedom, the translational degrees of freedom are restricted by "stiffness" simulated by using the motors of the robotic manipulator. FIG. 9A depicts this mode for an "engine manipulator" type of embodiment described below. As shown, joint angles of the manipulator may change in this mode, but the location of the fulcrum F remains unchanged.

Z Translate—In this mode, the manipulator arm is compliant in 1 or 2 degrees of freedom, along a single axis, and can be repositioned by the user by exerting force on the robotic arm. The robotic manipulator's motors are used to perform active gravity compensation such that the manipulator and payload float in space enabling the user to move the payload and manipulator without need to support the weight of the components. In this particular state, the arm and payload can be moved by the user, but the robotic arm will only allow the payload to be moved along the trocar axis (the longitudinal axis of the instrument) through the incision site and optionally rotate about the trocar axis, but not in any other translational or rotational degrees of freedom. All other degrees of freedom are restricted by "stiffness" simulated by using the motors of the robotic manipulator. FIG. 9B depicts this mode for an "engine manipulator" type of embodiment. As shown, joint angles of the manipulator may change in this mode, but the trocar (or, in the case of the FIG. 1-2 type embodiment, the instrument shaft) translates along its z axis (the insertion axis into the patient).

Payload Hold+Null Compliance—In this mode, the manipulator arm holds the payload (engine or instrument) stationary in space, while the manipulator arm itself is compliant. In this particular state, the arm can be moved by the user, but the payload cannot. This requires that the arm has more than 6 degrees of freedom built into the mechanical design (e.g. FIG. 2). As a result, the arm can hold the payload fixed in position and orientation while the arm itself is free to move. The user is able to push or pull the robotic arm into different positions without moving the end effector which may or may not be actively in use inside a patient. This allows the OR staff to move the arm to ensure that it is out of the way during a surgical intervention.

RCM Hand-guiding+Z Translate—In this mode, the manipulator arm is in a "compliant" state in which it can be repositioned by the user by exerting force on the robot, with some restrictions. The robotic manipulator uses the motors to perform active gravity compensation such that the manipulator and payload float in space enabling the user to move the payload and manipulator without need to support the weight of the components. In this particular state, the arm and payload can be moved by the user, but the robot will only allow the payload to rotate about a fixed control point and translate through that point along the trocar axis (4 degrees of freedom=1 translational+3 rotational). The instrument or engine (payload) can be rotated about the fulcrum point and moved along the trocar axis but cannot be translated in the other 2 degrees of freedom. The payload can only be manipulated in 4 degrees of freedom, the other 2 translational degrees of freedom are restricted by "stiffness" simulated by using the motors of the robotic manipulator. The fulcrum (control) point remains in a fixed position in space as the instrument or engine is moved along the trocar axis. This ensures that as an instrument moves in or out of the patient, the fulcrum point of rotation is still at the incision site, minimizing trauma to the patient during the procedure.

Wheels-unlocked mode to allow repositioning of the arm to another position or orientation on the operating room floor.

The system may be programmed to operate with varying levels of complexity depending on the number of gesture force inputs to be recognized by the system and the number of system functions that can be carried out based on gesture force inputs.

In a most simple example, gesture force input is used only to toggle an arm between two different states (e.g. enabled and disabled), configurations/poses or modes. In more complex examples, the programmed instructions map each gesture force input in a collection of gesture force inputs to each operational modes, functions, or operational states in a collection of modes/functions/operational states. As another example, the system may be programmed with a sequence of operational states, and the controller commands the system to advance from one operational state to the next operational state in the sequence each time gesture force input is received. For example, if the user wishes for the robotic arm to move from a first, storage configuration, to a second position more extended position more suitable for draping, the user may push twice on the robotic arm. The force and/or torque sensors in the manipulator will detect these forces and the controller can identify that this type of force applied while in the storage pose indicates that the robot should move to the draping position. After draping, the user might repeat the gesture force input, causing the robotic arm to position itself in the next position in the sequence, such as one in which the effector unit is positioned or configured for instrument attachment.

In a further modification of the prior example, the system is further programmed to move from one operational state to the previous operational state in the sequence in response to a second type of gesture force input.

Method

Figure 3:
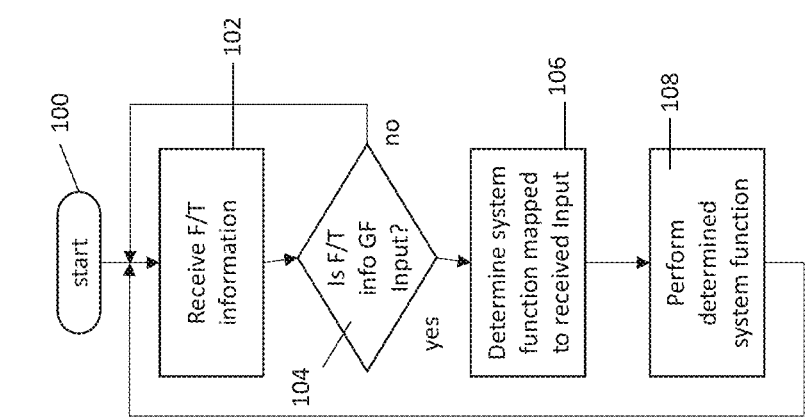
FIG. 3 is a flow diagram illustrating a first embodiment of a force-based gesture control method.

A first method of using the disclosed force-gesture control system will next be described with respect to FIG. 3. As a starting point, the gesture force input capability of the system is turned on. Step 100. In each exemplary method the system can be set up so that gesture force input capability is always activated when the surgical system is powered on, or it may be set up to require an additional act to place the system into a gesture force input mode. In the latter example, a user may place the system into gesture force input mode using an input action at the surgeon console (e.g. keyboard input, input at the HMI, eye tracking input, voice input, a button press on a handle 17, 18, touch input on a touch sensitive surface), at one of the robotic arms (e.g. a button press, touch input on a touch sensitive surface, voice command) or some other location.

With the system in gesture force input mode, a user applies a force gesture to the robotic manipulator to communicate the user's intent as to the function to be performed by the system, or as to the operational mode or state the user wants the system to enter. The controller receives force and/or torque ("F/T") information from the GFS in the corresponding robotic arm, Step 102, and determines whether the information is gesture force input. Step 104. An affirmative determination in Step 104 means that the F/T information satisfies the rules or parameters in the programmed instructions that define the information that is to be accepted by the system as gesture force input.

If the F/T information is determined to be gesture force input, the controller commands the system to perform the system function associated with that gesture force input. Step 108. If the system utilizes multiple forms of gesture force input for multiple system functions, Step 108 is preceded by an additional step of determining, using the programmed instructions, which system function is to be formed based on the form of gesture force input received. Step 106.

Figure 4:
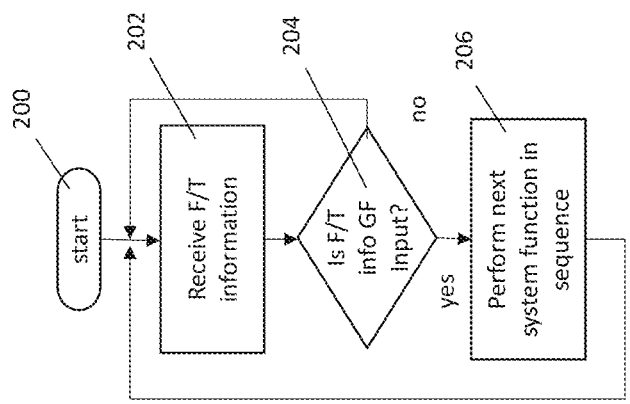
FIG. 4 is a flow diagram illustrating a second embodiment of a force-based gesture control method.

In a second method illustrated in FIG. 4, Steps 200-204 are similar to Steps 100-104 of the first method, but in the second method gesture force input is used to advance through a sequence of operational states. Once the F/T input is determined to be gesture force input (Step 204), the system advances from its current mode of operation/operational state to the next one in a predetermined sequence. Step 206.

A third method is similar to the second, but the third method includes the additional step (Step 306) of determining whether the gesture force input is the one programmed for forward or reverse advancement through the arm positions and/or modes/states of operation in the sequence. This allows bi-directional advancement of the system through a sequence of positions and/or operational states in response to gesture force input. Thus, the programming is set up to map a first type of gesture force input to forward advancement of the system through the sequence, and to map a second type of gesture force input to a reverse advancement of the system through the sequence.

As a non-limiting example of the third embodiment, the system may be programmed with a sequence of states that include a storage position, a draping position, an instrument mounting position, and a hand-guiding operational mode. A first gesture force input (e.g. 3 pushes in a 2 second period) is applied to the arm, and the controller causes the arm to move from the storage position to the draping position. After draping, the first gesture force input is repeated by the user, prompting the controller to cause the arm to move from the draping position to the instrument mounting position. If, prior to instrument mounting, the user determines that the arm must be returned to the draping position for adjustment of the drape or some other purpose, the user applies a second gesture force input that is different from the first gesture force input (e.g. 2 pushes in a 2 second period). The controller then causes the arm to return to the draping position. Once the drape has been adjusted, the user repeats the first gesture force input to cause the controller to again advance the sequence in the forward direction to return to the instrument mounting position and then, once the instrument is mounted, the user can once again repeat the first Gesture Force input. This prompts the controller to change the operational state of the arm 8 to the hand-guiding state, allowing the user to guide the arm to insert the tip of the instrument into the body cavity.

Additional Control Modes and Associated Features

Although the above control modes have been described as being initiated using gesture input, they can also be initiated using other forms of input used with surgical robotic manipulators. These functionalities and features could apply to single instrument manipulators of the type used for multi-port surgery, such as those shown in FIGS. 1 and 2, each of which includes an arm having a plurality of actuated joints. The arm supports a surgical instrument which is inserted into a patient via an incision. Actuators in the arm and/or instrument actuate features of the instrument, including opening/closing of jaws, articulation, end effector or shaft roll and the like.

Figure 6:
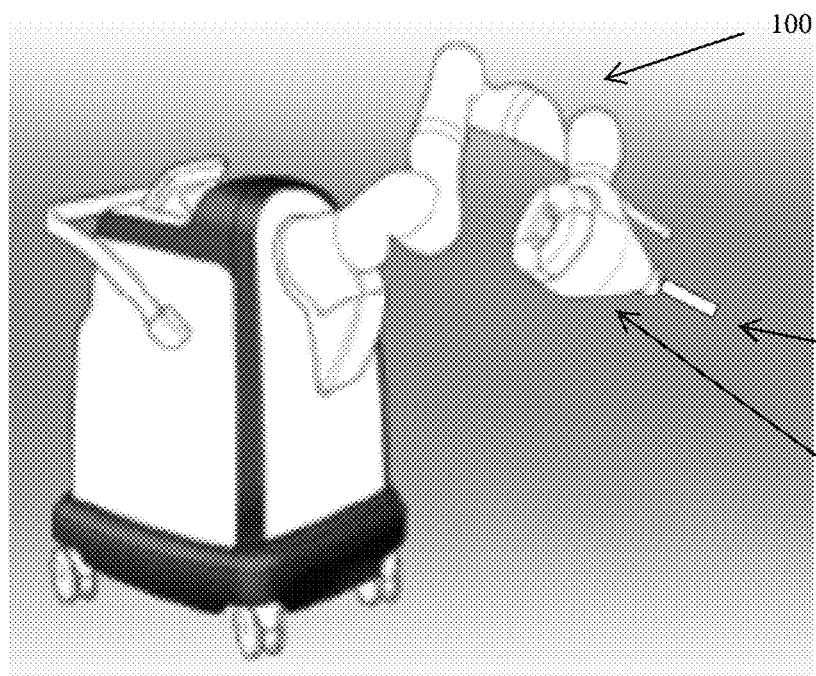
FIG. 6 illustrates a robotic manipulator system configured to support and manipulate more than one surgical instruments that extend through a common insertion tube or trocar inserted into the patient.

The functionalities and features described in this application can also be used for instrument engine manipulators in which more than one surgical instrument is carried by an "engine manipulator" 116 on a manipulator arm. The surgical instruments (not shown, but see instrument 114 being inserted into engine manipulator 116 in FIG. 7B) are engaged with or inserted through the engine manipulator and their distal ends are passed through an insertion tube 118 or trocar into the body cavity of a patient. Actuators of the engine manipulator control operation of the instruments within the patient's body cavity. This type of system is useful for single-port surgery. See also commonly owned WO2016057989 and WO2017/181163, each of which is incorporated herein by reference. In each of the above examples the arm 100 may include gravity loaded axes at its joints. Each arm may be mounted to a base having wheels as shown in FIG. 6.

Examples of control modes that may be entered using gesture input or other forms of input include those listed above, as well as the following. The modes will be described with respect to FIGS. 6 through 8C, but it should be understood that they are suitable for use in other types of robotic arm and instrument configurations, including the types described with reference to FIGS. 1 and 2.

Restricted Handguiding—In this mode, the manipulator arm 100 is in a "compliant" state in which it can be repositioned by the user by exerting force on the robot (handguiding). The robotic manipulator uses the motors to perform active gravity compensation such that the manipulator and payload float freely in space enabling the user to move the payload and manipulator without need to support the weight of the components. In this particular state, the arm and payload can be moved along a predefined path between the current position and a predefined destination position and orientation. This can be used to help the user put the payload and arm into a storage position, an optimal procedure start position, a draping position, or other useful position depending on application. This can be implemented either as a single or series of straight line paths, a single or series of curved line paths, or other, such that the guided motion is able to avoid collisions with the manipulator arm or mobile cart on which it may be mounted. Also, the path may either require that the user move along a precise curve with a high stiffness resisting deviation from the defined line, or potentially a very soft low stiffness resistance which would be more forgiving to deviations. Alternatively, the robot may allow motion within a "tube" rather than along a single curve or line path. This would allow the user to move within a defined zone, but resist motion beyond the defined boundaries.

Hypersensitive Compliance Mode for Patient Repositioning—This mode would behave similarly to the fully compliant mode described above, but be intended for use during patient repositioning. In order to minimize incision trauma during repositioning with a surgical device inside the patient, the robotic manipulator must allow the instrument to move with the patient. One possible way to accomplish this is to put the robotic manipulator into a compliance control mode, similar to the full compliance mode described previously, and allow the instruments to move with the patient during repositioning, potentially with assistance from the OR staff. In this mode, the robot is especially sensitive to external loads, so that motion is accomplished with minimal external load applied to ensure minimal patient trauma. To get this level of resolution on external loads, it may be preferred to gather force data using an additional force torque sensor rather than using the joint torque sensors in the robotic arm.

Sensor Guided Patient Repositioning—Another way to accommodate patient repositioning during the procedure is to have the robotic manipulator autonomously reposition the instrument (or engine) as the bed/patient is adjusted. To accomplish this, a sensor can be attached to the bed and/or patient during the procedure to sense the orientation of the bed. This information, along with the relative position of the sensor to the instrument being supported by the robotic manipulator can be used to determine the required motion of the instrument to minimize the relative motion between the instrument and the patient. This enables the manipulator arm to move the instrument as the bed/patient are repositioned such that the instrument does not move relative to the patient. In this mode, the robotic manipulator will autonomously detect the patient motion, and move to accommodate this travel.

Payload Tele-manipulation+Null Compliance—In this mode, the instrument or engine is moved by the robotic manipulator via the surgeon from a remote input console rather than by physical handguiding. As the surgeon manipulates the input device, the robotic manipulator moves to accomplish the desired position and orientation of the instrument or engine. In addition to this base capability, in this control mode, the robot has Null Compliance. This is similar to control mode 4, except that the null space compliance is also active while the payload is being manipulated remotely by the user. Because of the redundant degree(s) of freedom in the manipulator, the robotic manipulator can be repositioned without affecting the position or orientation of the instrument so as to be positioned out of the way during the procedure without affecting the work of the user at the remote input console.

In the various control modes listed in this application, particularly Fully Compliant, RCM Handguiding, Z translate, Payload Hold & Null Compliance, RCM Handguiding & Z Translate, Restricted Handguiding, Hypersensitive Compliance Mode for Patient Repositioning, and Sensor Guided Patient Repositioning, some of the manipulator components or axes may be supported by passive gravity compensation using mechanisms as an alternative to active gravity compensation using motor torque.

The following additional features may be used in conjunction with the control modes listed above:

Control Handle and Button—To control the transition between the various control modes and to handguide the manipulator in the compliant modes, a control handle with an activation button may be used, with the handle located on the manipulator arm or engine manipulator. See, for example, handle 122 shown in FIGS. 8B and 8C. Alternatively, the activation button might simply be on a location on the arm that would be touched by the user to move the arm. The desired control mode can be selected on an input device 124 (tablet, button, etc). According to one configuration, to transition into a compliant control mode, the user must grab the control handle, pressing a $1^{st}$ button (e.g. with his or her hand), and then press a $2^{nd}$ button (e.g. with a finger or thumb) to transition the manipulator into the compliant control mode. This ensures that the user is holding the handle before transitioning by having a redundant input button to avoid activation by accidental contact.

Procedural Start Points & Setup Optimization—As a method of maximizing the usability of the surgical device, predefined start points for the robotic manipulator can be used to ensure that the maximum range of motion, strength, stiffness, etc are available to the user. To accomplish this, the robotic manipulator can be pre-programmed with starting poses for each type of procedure and setup that may be performed with the device. For example, the user may use an input device to select the procedure to be performed, which side of the patient the robotic manipulator will be setup on, and other inputs about the patient setup, enabling the robotic manipulator to select the appropriate starting pose for optimal procedure performance. If sensors are used or incorporated into the trocar through which the surgical instrument(s) supported by the arm extend, this could also be accomplished without all of the user inputs about patient setup. In another embodiment the calculation method is programmed into the robotic manipulator and the system is configured to calculate the optimal starting pose based on the setup conditions rather than using a pre-programmed pose based on given discrete setup choices.

Figure 7A:
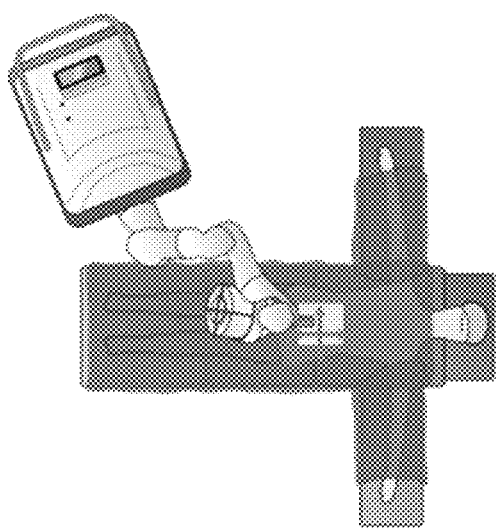
FIG. 7A illustrates the system of FIG. 6 with the trocar inserted into the patient.
Figure 7B:
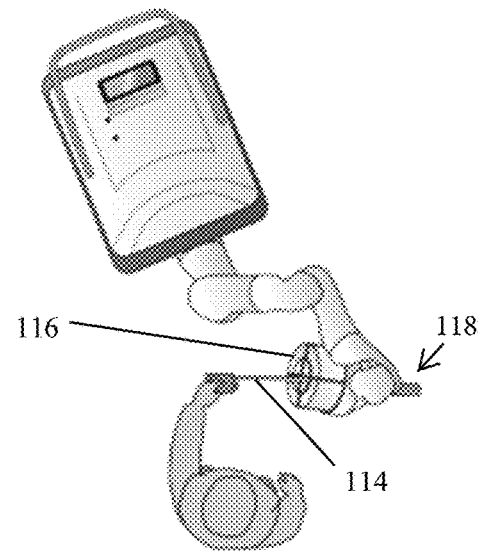
FIG. 7B illustrates the system of FIG. 7A, with a user inserting an instrument into the engine component.
Figure 8A:
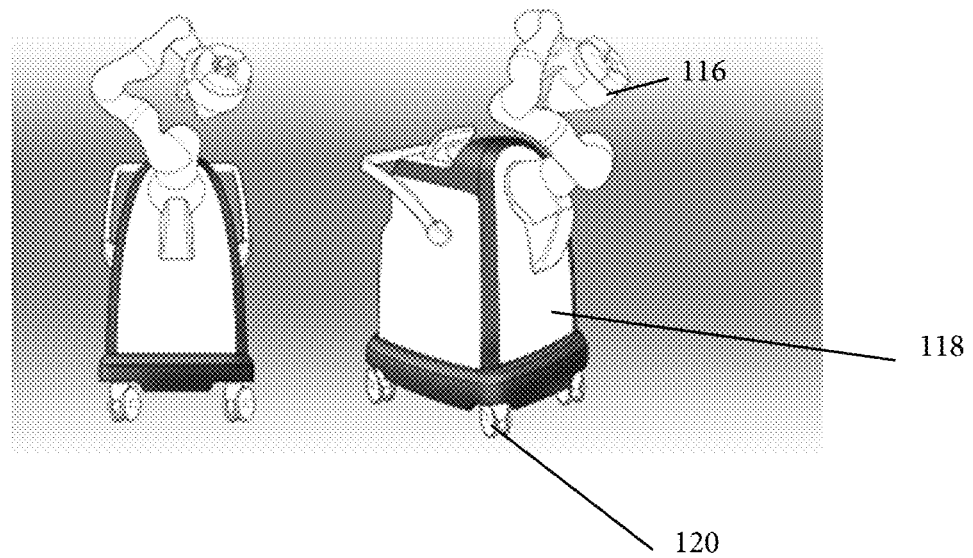
FIGS. 8A-8C show a sequence of use states for a surgical robotic manipulator.
Figure 8B:
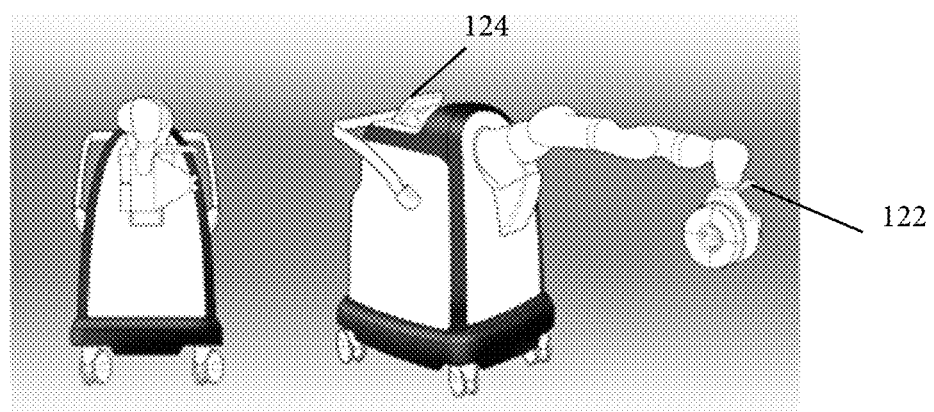
Figure 8C:
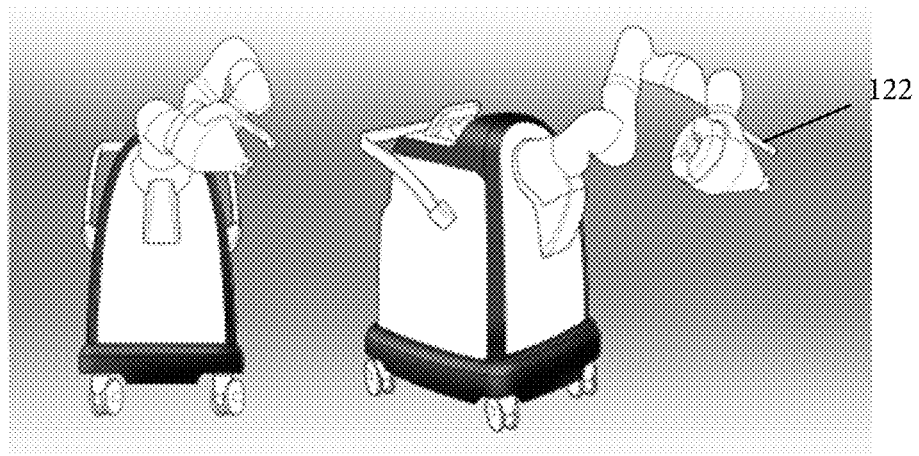

One particular example is a transition of the arm from a stowed position that configures the arm to be easily moved within the surgical suite or between surgical suites (e.g. a compact position as shown in FIG. 8A) to an extended position to allow surgical staff to more easily position a surgical drape on the arm (FIG. 8B). When in the stow position, the power of the robotic arm may be on or off, the brakes on the wheels of the arm are engaged, the brakes at the joints of the arm are engaged, no instruments are supported by the arm, and the arm is in a safe configuration for transport or storage. When the user enters input (using input on the arm itself or from a remote interface), the state of the arm is that the power is on, the brakes on the wheels are engaged, the brakes at the arm brakes are disengaged, no surgical instruments are mounted to the arm, and the arm is automatically extended for draping by activation of motors at the joints. A subsequent transition from the drape position to a home position (FIG. 8C) may then be carried out, where the home position is the neutral arm position. The arm may be configured to have different home positions, each intended for one or more particular surgical procedures. The state of the arm in the home position is that the power is on, the wheel brakes are engaged, the arm brakes are disengaged, surgical instruments have not yet been mounted, the arm is draped, and the arm joints are in a safe configuration for movement during the procedure. During each transition, gravity compensation features of the arm are activated. From this point, if the system is one of the type described in WO2016057989 where the system may be designed so that the distal part of the arm docks to the patient trocar 110, the arm 110 is subsequently docked to the trocar (FIG. 7A) (e.g. using a handguiding mode) and instruments are engaged with the arm and positioned extending through the trocar (FIG. 7B).

Actively Updated Gravity Compensation—During the procedure, the engine quadrants or other aspects of the surgical instrument are dynamically moved. This changes the position of the center of mass during use. Additionally, instruments can be added and removed throughout the use of the device. With gravity compensation, which is used in the compliant modes described previously, it is necessary to know the mass of the payload and the position of the center of mass so that the motors in the manipulator can exert the proper amount of torque/force to balance the weight of the payload. Therefore, to accommodate changes in the mass and center of mass of our surgical device, the manipulator must dynamically update the mass model used for gravity compensation during use. Sensors are used to detect which instruments and components are installed on the surgical device and also to detect the position of the moving components. This information is then used to determine the position of the center of mass, and update the gravity compensation model of the robotic manipulator.

Control Modes with Enhanced Safety and/or "Blending"—The goal of this feature is to reduce the risk associated with transitioning between a fixed position, in which the robotic manipulator is holding the instrument still, and a compliant state. If the instrument is under load, when the manipulator becomes compliant it could potentially move quickly due to these external forces. A few new capabilities can address these concerns. First, the manipulator has force/torque sensors and can detect the external loads applied. This information can be used to display on the user interface or monitor a warning or indication about the magnitude and direction of the external forces. This will enable the user to anticipate the external forces prior to engaging the control handle button and executing the control mode transition. Alternatively or additionally, the transition can be "blended" to reduce these risks. This feature will gradually reduce the "stiffness" of the robotic manipulator over time when the control button is pressed and the user intends to handguide the robot (<3 seconds). By transitioning in this way, the user can feel the intended motion of the manipulator and payload before the forces on the user become large, enabling the user to release the button if the behavior seems unexpected. This gradual blending between states enables safer operation of the device.

Dynamic Limit Avoidance & Alerts—These features aim at improving usability and safety. The robotic manipulator has limits to the range of motion of each axis, the amount of torque or force that can be exerted on each axis, the speed at which the payload can safely be moved, the space in which the payload can be moved, etc. To maximize the usability and safety of the manipulator, the robot can dynamically help avoid these hard limits and alert the user as they approach thresholds. As the manipulator axes approach the defined range of motion limits, the stiffness of each axis (in that direction) can be increased gradually as the robot gets closer to the limit. This could feel similar to pushing against a spring on the axis. This will cause the motion to be accomplished preferentially by less stiff axes with more available range of motion, enabling the desired compliant motion to continue. Similarly, as the user approaches the defined instrument speed limit, the damping of the robotic manipulator will increase gradually to prevent the user from exceeding this limit. The same concept is applied to the position of the payload in space. As the payload is moved closer to other parts of the manipulator or cart, the stiffness in that direction will increase, preventing collision with other objects. Visual and audible alerts can also be used to warn users. For example, if an axis is nearing the torque or force limit, an alert is provided to indicate that the forces should be reduced.

All patents and applications referred to herein, including for purposes of priority, are incorporated herein by reference.

I claim:
1. A surgical robotic system, comprising:
   a robotic manipulator arm configured for robotic positioning of a surgical instrument in a body cavity, the robotic manipulator arm including at least one force sensor;
   at least one user input device remote from the robotic arm;
   a robotic system controller responsive to input from the user input device to move the robotic manipulator during a surgical procedure; and a processor;

wherein the force sensor is positioned to generate first force signals in response to gesture force input applied directly by a user to the body of the robotic manipulator and the robotic system controller is further responsive to said first force signals to cause movement of the manipulator arm to a predetermined pose or position; and wherein the force sensor is positioned to generate second force signals in response to forces exerted on the surgical instrument during movement of the surgical instrument in a body cavity, and wherein the processor is configured to provide haptic feedback signals to the user input device based on the second force signals during a surgical procedure.

2. The system of claim 1, wherein the predetermined pose or position is a storage configuration.

3. The system of claim 1, wherein the predetermined pose or position is a draping configuration.

4. The system of claim 1, wherein the predetermined pose or position is an instrument attachment configuration.

5. The system of claim 1, wherein the predetermined pose or position is a home configuration.

6. The system of claim 1, wherein the robotic arm includes an effector unit, the instrument attachable to the effector unit, and wherein the force sensor is a 6 DOF force/torque sensor fixed to the effector unit.

7. The system of claim 1, wherein the robotic arm includes a plurality of joints, and wherein the force sensor comprises a plurality of force/torque sensors at said joints.

8. A method of controlling a robotic arm, comprising:

manually applying a force to a body of a robotic arm;

receiving first force information from a force sensor on the robotic arm;

determining, using the first force information, whether the force is a gesture force input;

if the force is a gesture force input, initiating electromechanical movement of the manipulator arm to a predetermined pose or position;

manipulating a user input device remote from the robotic arm to generate user input, and moving the robotic arm in response to the user input to manipulate a surgical instrument within a body cavity; and during the step of moving the robotic arm in response to the user input, receiving second force information from the force sensor and, providing haptic feedback signals to the user input device based on the second force information.

9. The method of claim 8, wherein the predetermined pose or position is a storage configuration.

10. The method of claim 8, wherein the predetermined pose or position is a draping configuration.

11. The method of claim 8, wherein the predetermined pose or position is an instrument attachment configuration.

12. The method of claim 8, wherein the predetermined pose or position is a home configuration.

* * * * *